(12) United States Patent
Sagara

(10) Patent No.: US 6,586,524 B2
(45) Date of Patent: Jul. 1, 2003

(54) CELLULAR TARGETING POLY(ETHYLENE GLYCOL)-GRAFTED POLYMERIC GENE CARRIER

(75) Inventor: Kazuyoshi Sagara, Buzen (JP)

(73) Assignee: Expression Genetics, Inc., Sandy, UT (US)

(*) Notice: Subject to any disclaimer, the term of this patent is extended or adjusted under 35 U.S.C. 154(b) by 0 days.

(21) Appl. No.: 09/909,418

(22) Filed: Jul. 19, 2001

(65) Prior Publication Data

US 2003/0018002 A1 Jan. 23, 2003

(51) Int. Cl.$^7$ ............................................. C08F 283/06
(52) U.S. Cl. ................. 525/54.11; 525/409; 525/326.8; 424/94.3; 435/320.1; 435/188; 528/374; 530/300; 530/326; 530/350; 530/387.5; 514/44
(58) Field of Search ................. 525/54.11, 60, 525/409, 50, 54.1; 424/94.3; 435/188, 320.1; 528/374; 530/300, 322, 350, 387.5; 536/23.1, 24.2; 514/44

(56) References Cited

PUBLICATIONS

MJ Lentz et al., Proceed.Int'l.Symp.Control.Rel.Bioact.Mater., "Synthesis and Characterization of a Poly–L–Lysine–Polyethylene Glycol–Lactose Delivery Vehicle for Gene Delivery," Jul. 1999, 26, pp. 809–810.*

T Blessing at al.,Bioconjugate Chem., "Different Strategies for Formation of PEGylated EGF–Conjugated PEI/DNA Complexes for Targeted Gene Delivery," 2001, 12, pp. 529–537.*

M Morpurgo et al., Bioconjugate Chem. "Preparation and Characterization of Poly(ethylene glycol) Vinyl Sulfone," 1996, 7, pp. 363–368.*

O. Boussif, F. Lezoualc'h, M.A. Zanta, M.D. Mergny, D. Scheman, B. Demineix, J. P. Behr, A Versatile Vector for Gene and Oligonuclcotide Transfer into Cells in Culture and in Vivo: Polyethylenimine. Proc. Natl Acad. Sci. U.S.A. 92 (1995) 7297–7301.

D. G. Miller et al., Gene Transfer by Retrovinus Vectors Occurs Only in Cells that are Actively Replicating at the Time of Infection. 10 Mol. Cell Biol. 4239–4242 (1990).

M.A. Wolfert et al, Characterization of Vectors for Gene Therapy Formed by Self–Assembly of DNA with Synthetic Block Co–Polymers. 7 Hum. Gene. Ther. 2123–2133 (1996).

(List continued on next page.)

Primary Examiner—James Ketter
Assistant Examiner—M B. Marvich
(74) Attorney, Agent, or Firm—Thorpe North & Western, LLP

(57) ABSTRACT

The present invention relates to cationic polymeric conjugates and methods of preparing and using them as gene carriers. The cationic polymeric conjugates comprise a poly(ethylene glycol) (PEG) grafted cationic polymer and a targeting moiety(TM), wherein 0.1 to 10 mole percent of the cationic groups of the cationic polymer are substituted with PEG-TM.

29 Claims, 9 Drawing Sheets

OTHER PUBLICATIONS

J. C. Perales et al., An Evaluation of Receptor–Mediated Gene Transfer Using Synthetic DNA–Ligand Complexes. 226 Eur. J. Biochem., 255–266 (1994).

Model Nucleoprotein Complexes: Studies on the Interaction of Cationic Homopolypeptides with DNA. 24 J. Mol. Biol., 157–176 (1967).

T. D. McKee et al., Preparation of Asialoorosomucoid–polylysine Conjugates. 5 Bioconj. Chem., 306–377 (1994).

G. Ross et al., Gene Therapy in the United States: A Five–Year Status Report. 7 Hum. Gene Ther., 1781–1790 (1996).

T. Bettinger, J.S. Remy, P. Erbacher, Size Reduction of Gatactosylsted PEI/DNA Complexes Improves Lectin–mediated Gene Transfer into Hepatocytes. Bioconjugate Chem. 10 (1999) 558–581.

M. A. Zanta, O. Boussif, A. Adib, J. P. Behr, In Vitro Gene Delivery to Hepatocytes With Galactosylated Polyethylenimine. Bioconjugate Chem. 8 (1997) 839–844.

A. V. Kabanov & V. A. Kabanov DNA Complexes with Polycations for the Delivery of Genetic Materials into Cells. 6 Bioconj. Chem., 7–20 (1996).

S. Gottschalk et al., A Novel DNA–Peptide Complex for Efficient Gene Transfer and Expression in Mammalian Cells, 3 Gene Ther. 448–457 (1996).

P. Erbacher, T. Bettinger, P. Belguise–Valladier, S. Zou, J. L. Coll, J. P. Behr, J. S. Remy, Transfection and Physical Properties of Various Saccharide Poly(ethylene Glycol), and antibody–derivatized Polyethylenimines OPEI), J. Gene Med. 1 (1999) 210–222.

* cited by examiner

CELLULAR TARGETING POLY(ETHYLENE GLYCOL)-GRAFTED POLYMERIC GENE CARRIER

BACKGROUND OF THE INVENTION

This invention relates to targeted gene delivery. More particularly, the invention relates to a composition comprising a conjugate of poly(ethylene glycol)-grafted cationic polymers, i.e. polyamines, and a cell targeting molecule for gene delivery to the target cells.

Gene therapy has represented a new paradigm for therapy of human disease and for drug delivery. The implicit emphasis of prior research has been on determining the safety of gene transfer procedures, often placing efficacy as a secondary goal. A major technical impediment to gene transfer is the lack of an ideal gene delivery system. If it were possible to deliver the gene to the appropriate specific cells in sufficient quantities without adverse side effects, gene therapy would be efficacious. Currently very few organs or cells can be specifically targeted for gene delivery.

There are many established protocols for transferring genes into cells, including calcium phosphate precipitation, electroporation, particle bombardment, liposomal delivery and viral-vector delivery. Although all of these methods can be used for mammalian cultured cells, there are many difficulties in introducing genes into target cells in vivo.

Transfection methods using retroviral or adenoviral vectors overcome some of these limitations. Retroviral vectors, in particular, have been used successfully for introducing exogenous genes into the genomes of actively dividing cells such that stable transformants are obtained. D. G. Miller et al., Gene Transfer by Retrovirus Vectors Occurs Only in Cells that are Actively Replicating at the Time of Infection. 10 Mol. Cell Biol. 4239–4242 (1990). Viral vector systems often involve complementation of defective vectors by genes inserted into 'helper' cell lines to generate the transducing infectious agent. However, it is well known that the host immune response to adenoviruses limits their use as a transfer facilitating agent to a single administration. To address this limitation fusion peptides of the influenza virus hemagglutinin have been employed to replace adenoviruses as endosomal lytic agents, but they have met with limited success. S. Gottschalk et al., A Novel DNA-Peptide Complex for Efficient Gene Transfer and Expression in Mammalian Cells, 3 Gene Ther. 448–457 (1996). However, despite their high transfection efficiency in vitro, inserting genes into the host cell's genome in this method depends on the viral infection pathway. Application of the viral infection pathway for human gene therapy introduces serious concerns about endogenous virus recombination, oncogenic effects, and inflammatory or immunologic reactions. G Ross et al., Gene Therapy in the United States: A Five-Year Status Report. 7 Hum. Gene Ther., 1781–1790 (1996). Because of these concerns, the use of viral vectors for human gene therapy has been extremely limited.

On the other hand, non-viral gene delivery systems such as cationic liposomes or synthetic cationic polymers, e.g.poly-L-lysine (PLL) and polyamines, are being widely sought as alternatives. M. A. Wolfert et al., Characterization of Vectors for Gene Therapy Formed by Self-Assembly of DNA with Synthetic Block Co-Polymers. 7 Hum. Gene. Ther., 2123–2133 (1996); A V Kabanov & V A Kabanov DNA Complexes with Polycations for the Delivery of Genetic Materials into Cells. 6 Bioconj. Chem., 7–20 (1995). There are several advantages to the use of non-viral based gene therapies including their relative safety and low cost of manufacture. The major limitation of plasmid DNA (pDNA)-based approaches has been that both the efficiency of gene delivery to important somatic targets (i.e., liver, lung and tumors) and in vivo gene expression levels are lower using non-viral approaches than those using viral vectors. Polyethylenimine (PEI), one of the most commonly used cationic polymers, mediates a high degree of transfection due to the release of pDNA from the endosome to the cytosol. O.Boussif, F. Lezoualc'h, M. A. Zanta, M. D. Mergny, D. Scherman, B. Demeneix, J. P. Behr, A versatile vector for gene and oligonucleotide transfer into cells in culture and in vivo: Polyethylenimine. Proc. Natl. Acad. Sci. USA. 92 (1995) 7297–7301. Although PEI condenses pDNA into complexes of less than 50 nm in salt-free buffer, these complexes aggregate immediately under physiological conditions such as in salt or bovine serum albumin.

Receptor-mediated gene delivery has its advantages and limitations. Its advantages for use in gene therapy are as follows. First, the gene delivery carrier can be designed and customized for a specific target receptor. Second, the DNA does not have to integrate into the host cell genome to be expressed. Third, the delivery system is theoretically not limited by the size of the transgene. Finally, the technique does not involve the use of potentially infectious agents. There are also disadvantages that must be overcome before this procedure can be routinely used for human gene therapy. For example, the transgene is not integrated into the host cell chromosomes, or its expression is transient. Therefore, it will most likely be necessary to subject patients to multiple injections of a gene of interest. The DNA-targeting moiety (TM) complexes are difficult to prepare and, until recently, little was known about their structure-function relationship. Also, there is only a fragmentary understanding of the biological process involved in the transfer of the transgene into the cell and its subsequent expression. These and other features of this system for gene therapy have recently been reviewed in detail. J. C. Perales et al., An Evaluation of Receptor-Mediated Gene Transfer Using Synthetic DNA-Ligand Complexes. 226 Eur. J. Biochem., 255–266 (1994).

Cationic polymers such polyamine and PLL can be used as a DNA condensate. However, the use of cationic polymers alone as gene delivery carriers has several disadvantages. First, transfection efficiency is very low because they have no functional group except the amine group used in charge-neutralization. Also, due to the negative charges of the DNA phosphate backbone, an increase in the degree of charge neutralization of the DNA often results in extensive condensation and the separation of the DNA phase in the form of insoluble compact structures. Nucleoprotein Complexes: Studies on the Interaction of Cationic Homopolypeptides with DNA. 24 J. Mol. Biol., 157–176 (1967).

The asialoglycoprotein receptor mediates internalization of proteins bearing galactose-terminated oligosaccharide moieties into hepatocytes in liver. Therefore, the combination of a polymeric gene carrier with ligands such as galactose(Gal), lactose(Lac), and apoprotein E has been studied to deliver genes into hepatocytes. Although ligands directly conjugated to PEI with 5% galactose gave high transfection rates in hepatocyte-derived cell lines, they were unable to prevent aggregation under physiological saline conditions. Researchers have tried to combine pegylation and galactosylation for synthesis of new polymeric gene carriers using PEI. However, these synthesis methods seem too complex and these products show low gene expression due to less than optimal galactosylated content. P. Erbacher, T. Bettinger, P. Belguise-Valladier, S. Zou, J. L. Coll, J. P.

Behr, J. S. Remy, Transfection and physical properties of various saccharide, poly(ethylene glycol), and antibody-derivatized polyethylenimines (PEI). J. Gene Med. 1 (1999) 210–222.

In view of the foregoing, it will be appreciated that providing a targeted composition of gene therapy and a method making thereof would be a significant advancement in the art.

BRIEF SUMMARY OF THE INVENTION

The present invention provides a composition that efficiently mediates DNA delivery into a target cell. The present invention further provides a biocompatible composition for efficient DNA delivery which causes non-cytotoxic transfection into a target cell.

The present invention relates to compositions containing a cationic polymer(CP), i.e. a polyamine(PA), having a certain percentage of its cationic functional groups grafted with poly(ethylene glycol)(PEG) which is in turn covalently bound to a targeting moiety(TM). One embodiment of the present invention relates to Gal-PEG-PEI for gene delivery to hepatocytes. Furthermore, this composition mediates transfection of DNA or gene moieties into human cells. This transfection method and composition accomplish these goals while presenting minimal cell toxicity and significantly increased transfection efficiency.

Accordingly, the TM-PEG-CP conjugates of the present invention were synthesized by coupling the TM to an end of a PEG chain and covalently attaching or grafting the other end of the CP thus formed TM-PEG-CP. Particularly, the method comprising obtaining a TM derivative having an amine group and PEG containing a λ-vinyl sulfone(VS) at one terminal and ω-N-hydroxysuccinimidyl esters(NHS) at the other terminal, reacting the amine group of the TM with the VS group of the VS-PEG-NHS to obtain VS-PEG-TM; and then reacting the VS group of the VS-PEG-TM with the amine groups of the PA at a pH value of 4 to 9, preferably 6–9. The cationic polymer is preferably a polyamine(PA) such as polyalkylenimine(PAI) or PEI, and the targeting moiety is preferably lactose or galactose. The ratio of TM-PEG and polyamine(PA) can be adjusted by changing the ratio of reaction concentrations. The synthesized carrier, namely TM-PEG-PA, wherein 0.1 to 10 mole percent of the cationic groups on the CP are conjugated with TM-PEG with the rest of the cationic groups remaining unsubstituted, is capable of forming a stable and soluble complex with a nucleic acid, which in turn is capable of efficient transfection. The TM-PEG moiety grafted to a CP resulted in better solubility and reduced cytotoxicity of the nucleic acid/carrier complex as compared to CP alone. Compared with a CP without TM-PEG, the TM-PEG grafted PEI of this invention provides for high solubility of the complexes formed with DNA in physiological serum and cell culture medium, and prevents the precipitation and aggregation of the complexes formed, and thus is capable of being administrated in vivo at very high doses. The gene transfection efficiency and cytotoxicity of the TM-PEG-PLL system were investigated and compared to those of DNA complexed with a CP, such as PEI alone. HepG2 cells, as model cell lines of hepatocytes, were transfected specifically with a pDNA/Gal-PEG-PEI complex, indicating that galactose serves as a targeting moiety for hepatocytes. The TM-PEG-PEI of this invention also decreases the proteolytic degradation of DNA in the circulatory system and in cells, and enhances the uptake of the DNA/polymer complexes thus improving transfection efficiency. In addition, PEG also functions as a linker connecting the PEI backbone and the targeting moiety, thus increasing the targeting efficiency of DNA delivery to the target cells.

DETAILED DESCRIPTION OF THE INVENTION

Figure 1:
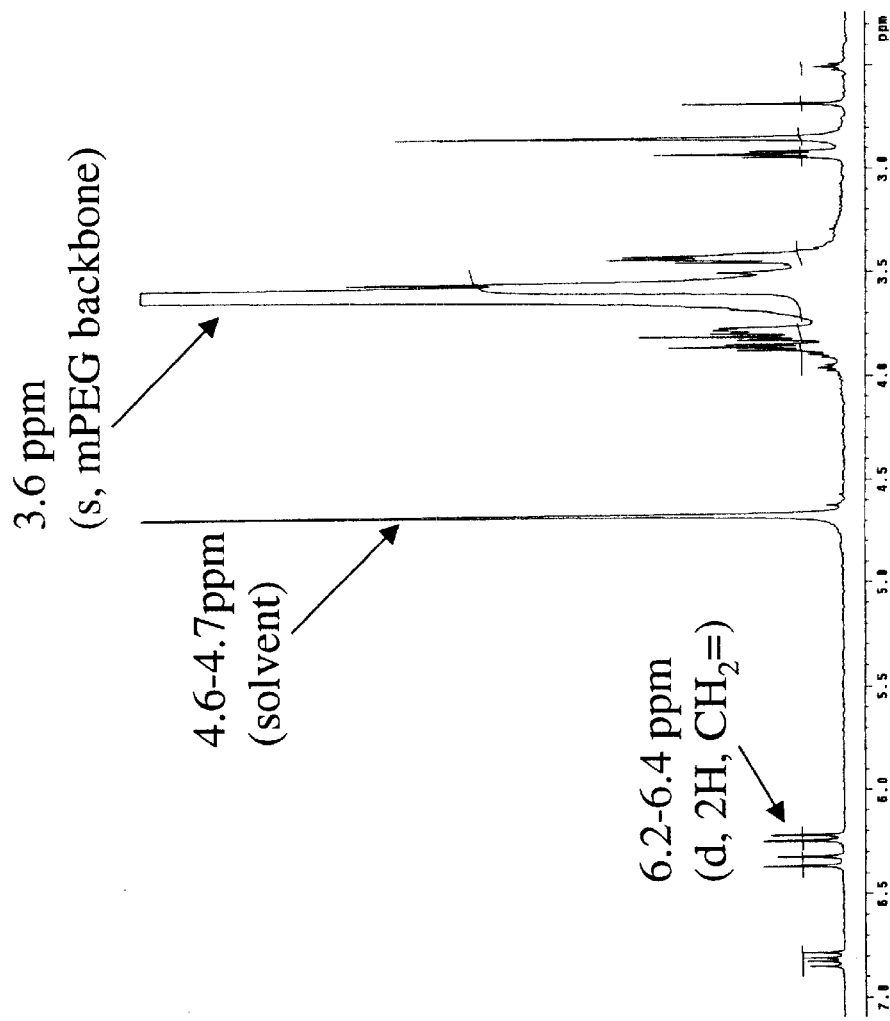
FIG. 1 is a depiction of an illustrative $^1$H-NMR spectrum (400 $MH_z$) analysis of VS-PEG-NHS in deuterium oxide ($D_2O$).

Before the present composition and method for gene delivery are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

This invention relates to a composition capable of forming stable, soluble complexes with nucleic acids and the method of preparation thereof comprising a cationic polymer(CP) member having a certain percentage of its cationic functional groups grafted to a poly(ethylene glycol) member (PEG), which is in turn covalently bound to a targeting moiety(TM) which is recognizable by cell membrane receptors. The cationic polymer can be a branched, linear, dendrimer, or block copolymer of a polyamine, preferably a PAI or PEI, and the targeting moiety is preferably lactose or galactose which selectively targets a hepatocyte. Preferably, 0.1 to 10 mole % of the amine groups of the polyamines are substituted by a PEG-TM, with 0.5–2 mole % being substituted being most preferred. The complexes are able upon dissociation to release the nucleic acid to transfect several types of cells and the TM makes the transfection selective to cells containing receptors for the TM. This invention also provides a method for specific cell transfection in vitro or in vivo.

The invention, in one of its most general definitions, concerns a complex between at least one negatively charged nucleic acid and at least one positively charged polymeric conjugate, the association between the nucleic acid and the polymeric conjugate being electrostatic in nature, said positively charged polymeric conjugate consisting essentially of a polyamine such as PAI or PEI, and a TM conjugated PEG, wherein about 0.1 to 10 mole % of the primary, secondary, or tertiary amine groups on the polyamine (1.8–800K Da) are covalently linked to PEG(0.25–35K Da), which is in turn covalently linked to a TM. The gene carrier of this invention allows a condensation of the DNA to remain very strong as the result of a cooperative phenomenon between the positive charges of the polyamine and the negative charges of the nucleic acid. In addition, the addition of PEG on part of the amine groups of the cationic polymer prevents precipitation and aggregation of the complexes formed by the polymer and nucleic acid, thus increasing the solubility of the complexes. The PEG also functions to increase the transfection efficiency. Furthermore, since PEG can serve as a linker connecting the cationic polymer backbone and the targeting moiety(TM), it increases the targeting efficiency of the complexes.

In the composition of this invention, the targeting moiety (TM) could be any signal member which is recognizable by a receptor on the cell membrane, preferably, the TM is a sugar moiety which specifically binds hepatocytes or non-parenchymal cells in liver. Examples of the sugar moiety includes: monosaccharides, oligosaccharides such as galactose, N-acethylgalactosamine and lactose; linear di-, tri-, tetragalactose; terminal sugar residues including di-, tri-, tetra-antennary sugar; polysaccharides and fructose, mannose terminal monoglycosides. Preferably, the sugar moiety is a member selected from the group consisting of lactose and galactose. In addition to sugar moieties, the TM may also be a targeting peptides, proteins or their domains such as lipoprotein(LDL), apoprotein E, or antibodies.

The composition of the invention can form stable and soluble complexes with nucleic acids which can effectively transfect mammal cells. The nucleic acid can be chosen from among the following items: a) gene markers, such as luciferase gene, β-galactosidase gene, chloramphenicol acetyl transferase gene, genes bestowing the resistance to an antibiotic, such as hygromycin or neomycin; b) genes for therapeutic purposes, such as the gene encoding low density lipoprotein receptors, deficient in the case of hypercholesterolemia (liver), coagulation factors, gene suppressers of tumors, major histocompatibility proteins, antioncogenes, sense and antisense RNA, and ribozymes; and c) genes with vaccine purposes, such as genes encoding viral antigens.

The PEG employed in the present invention has a MW from 0.25 to 35 K, preferably, 0.25 to 10K Da.

The cationic polymer employed in the present invention has a MW from 1.8 to 800K, preferably 2 to 30K. PAI or PEI are the preferred cationic polymers.

One embodiment of the present invention relates to a composition comprising a plasmid DNA and a galactose conjugated cationic polymer, for example, Gal-PEG-PEI.

The plasmid carrying the intended gene was delivered into the targeted liver cells using the composition of the present invention with enhanced transfection efficiency compared to that of PEI alone. It was shown from band retardation assays (FIG. 8) that Gal-PEG-modified PEI has the ability to form complexes with a p DNA. The shift of the pDNA/Gal-PEG-PEI band during electrophoresis depends on the pDNA:Gal-PEG-PEI ratio, which alters the complex net charge as well as its size and density. A. V. Kabanov & V A Kabanov, DNA Complexes with Polycations for the Delivery of Genetic Materials into Cells. 6 Bioconj. Chem., 7–20 (1995). The decrease in electrophoretic mobility of the pDNA/Gal-PEG-PEI complex was accompanied by an increase in the content of Gal-PEG-PEI in the system, and is due to neutralization of the DNA negative charge by the carrier positive charge. Formation of a DNA-carrier complex was also observed in a dye displacement assay.

The method of in vitro or in vivo transfection of the present invention includes the introduction of a complex of nucleic acids and a TM-PEG grafted cationic polymeric carrier into a medium containing cells to be transfected under conditions such that there exists:

passage of the complex from the medium into the plasma membrane of the cells, release of the nucleic acid of the aforementioned complex into the cytosol of the cells, transcription and expression of the nucleic acid in the transfected cells.

As discussed earlier, one of the problems of using unmodified cationic polymers as gene carriers is that complexation between the cationic polymer and DNA frequently results in formation of fine precipitates, limiting the concentration that can be used. T. D. McKee et al., Preparation of Asialoorosomucoid-polylysine Conjugates. 5 Bioconj. Chem., 306–311 (1994). Accordingly, complexation of pDNA with an unmodified cationic polymer such as PEI in 20 mM HEPES (pH 7.4) with 0.15 M NaCl resulted in precipitates at 50 μg/mL of pDNA, whereas the, TM-PEG-PEI of the present invention maintained the solubility of pDNA when they made complexes with DNA at this concentration. Therefore, it is apparent that the attached PEG moiety makes the pDNA/gene carrier complexes substantially more soluble and thereby more functional.

The invention also refers to a process for the preparation of the composition of a TM-PEG grafted cationic polymer to be used as a polymeric gene carrier as described above. As an example, the process for synthesizing Gal-PEG-PEI is described in the FIG. 5 and Example 5.

The invention also refers to the use of a complex formed by a nucleic acid and the polymeric gene carrier according to the present invention used for the transfection of cells which may be chosen from the following: cells from hematopoietic strains; liver cells; cells of skeletal muscles; skin cells such as fibroblasts, keratinocytes, dendritic cells, or melanocytes;

cells of the vascular walls such as endothelial cells or smooth muscle cells; epithelial cells of the respiratory tract; cells of the central nervous system; cancer cells; cells of the immune system, such as lymophocytes, macrophages, NK cells, etc.

The gene delivery ability of the synthesized carriers, Gal-PEG-PEI, as an example of the present invention and its specificity were investigated. HepG2 cells (human hepatocarcinoma cells) were chosen for the specificity test because they have specific asialoglycoprotein receptors on their surface as model cells of hepatocytes. The recognition of galactose is mediated by asialoglycoprotein receptors on liver cells. They are used for removal of glycoproteins from the blood. Many newly synthesized glycoproteins, such as immunoglobulins and peptide hormones, contain carbohydrate units with terminal sialic acid and galactose residues. During hours or days, depending on the particular protein, terminal sialic acid residues are removed by sialylases on the surface of blood vessels. The exposed galactose residues of these trimmed proteins are detected by the asialoglycoprotein receptors in the plasma membranes of hepatocytes in liver. The complex of the asialoglycoprotein and its receptor is then internalized by endocytosis into the hepatocytes. The present disclosure shows that the galactose moiety on the carrier can serve as a targeting material for the hepatocytes.

Figure 5:
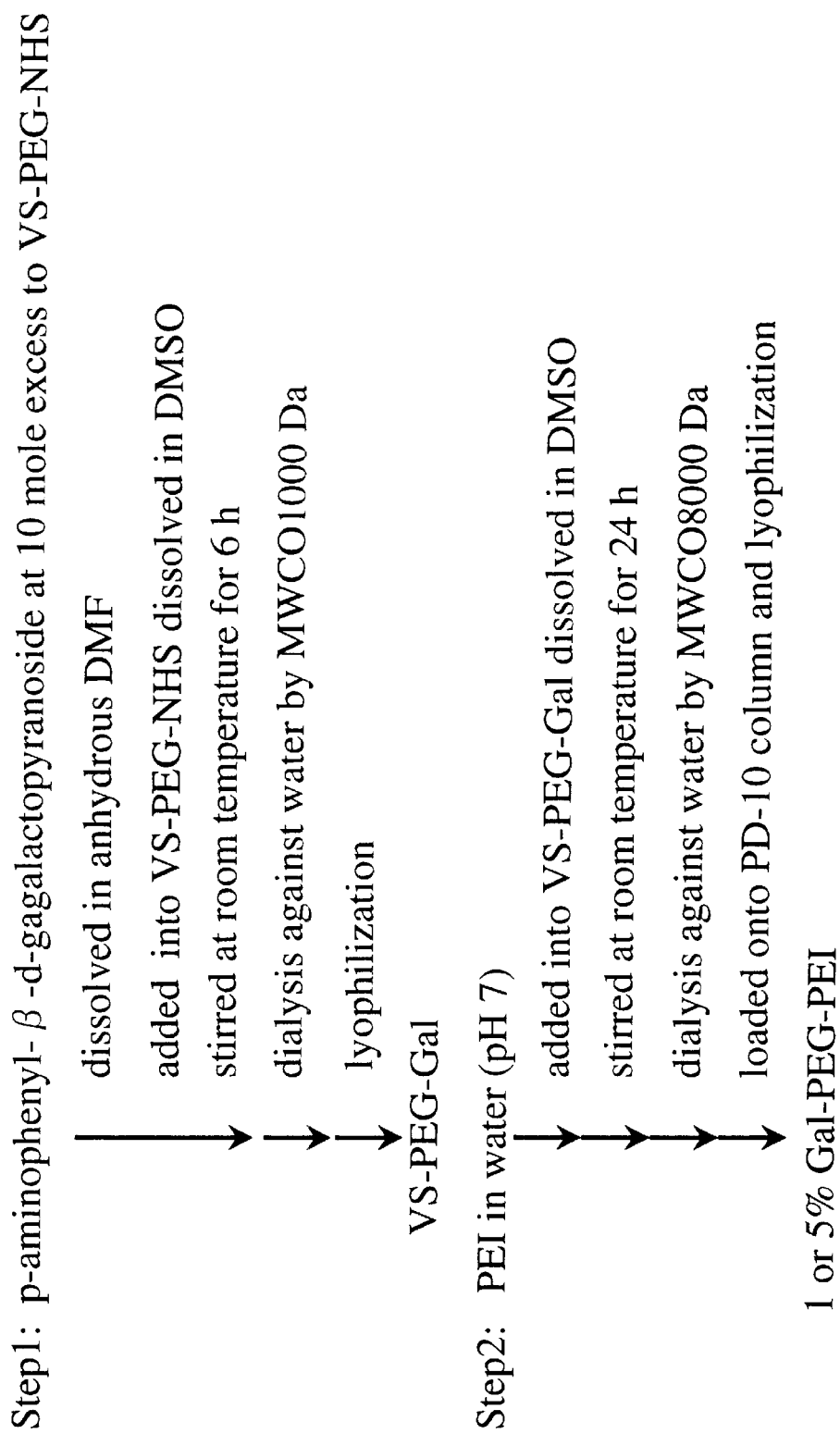
FIG. 5 shows the scheme for synthesis of Gal-PEG-PEI.

Gal-PEG-PEI was synthesized by a scheme comprising only two reactions, synthesis of VS-PEG-Gal and synthesis of the comb-shaped polymer 1 or 5% Gal-PEG-PEI from VS-PEG-Gal and PEI (FIG. 5). The Gal-PEG-PEI polymers of this invention make a complex with nucleic acids which makes the complex soluble, while the complex formed between a nucleic acid and a unmodified PEI forms a fine precipitate. The Gal-PEG-PEI carrier/DNA complex has superior transfection efficiency on HepG2 cells compared to that of a nucleic acid unmodified PEI complex. This increase may be due to the cell targeting effect of the galactose moiety. The attached PEG group also allows the Gal-PEG-PEI and the pDNA/Gal-PEG-PEI complex to be less cytotoxic than PEI alone. The galactose moiety specifically serves as a targeting moiety for transfection into hepatocytes. This was demonstrated by two pieces of evidence. First, free galactose at millimolar concentrations inhibited transfection. Second, very low transfection efficiency was noted when asialoglycoprotein receptor-deficient cell lines were used for transfection. The existence of FBS and chloroquine improved transfection further demonstrating that transfection occurred via an endocytosis mechanism.

In order to achieve specific targeting to hepatocytes using the asialoglycoprotein receptor, an optimal density of Gal-PEG units should be conjugated with the synthetic cationic polymers. The optimal percentage of galactosylation was reported to be 5% of the total amine functions in PEI in order to show high transfection in human hepatocyte-derived cells lines (HepG2). T. Bettinger, J. S. Remy, P. Erbacher, size reduction of galactosylated PEI/DNA complexes improves lectin-mediated gene transfer into hepatocytes. Bioconjugate Chem. 10 (1999) 558–561.M. A. Zanta, O. Boussif, A. Adib, J. P. Behr, In vitro gene delivery to hepatocytes with galactosylated polyethylenimine. Bioconjugate Chem. 8 (1997) 839–844. However, the direct conjugation to PEI with monosaccharides was too weak to prevent aggregation of the complexes with pDNA in physiological saline. These results suggested that bearing a sugar moiety somewhat interferes with electrostatic condensation between pDNA and PEI. In addition, increasing spacer distances between sugar moieties improved affinity binding to the asialoglycoprotein receptors by the formation of cluster glycosides. If sugar moieties at the terminal site of PEG were prevented from being buried inside the polymer/pDNA complexes, the use of PEG as a spacer could improve both condensation and attachment to asialoglycoprotein receptors on target cells. The present invention provides a new method of synthesis of PEI derivatives with 1 and 5% terminal galactose-grafted PEG (Gal-PEG-PEI) which protect against aggregation under physiological conditions and still bear sufficient targeting sugar moieties.

Figure 2:
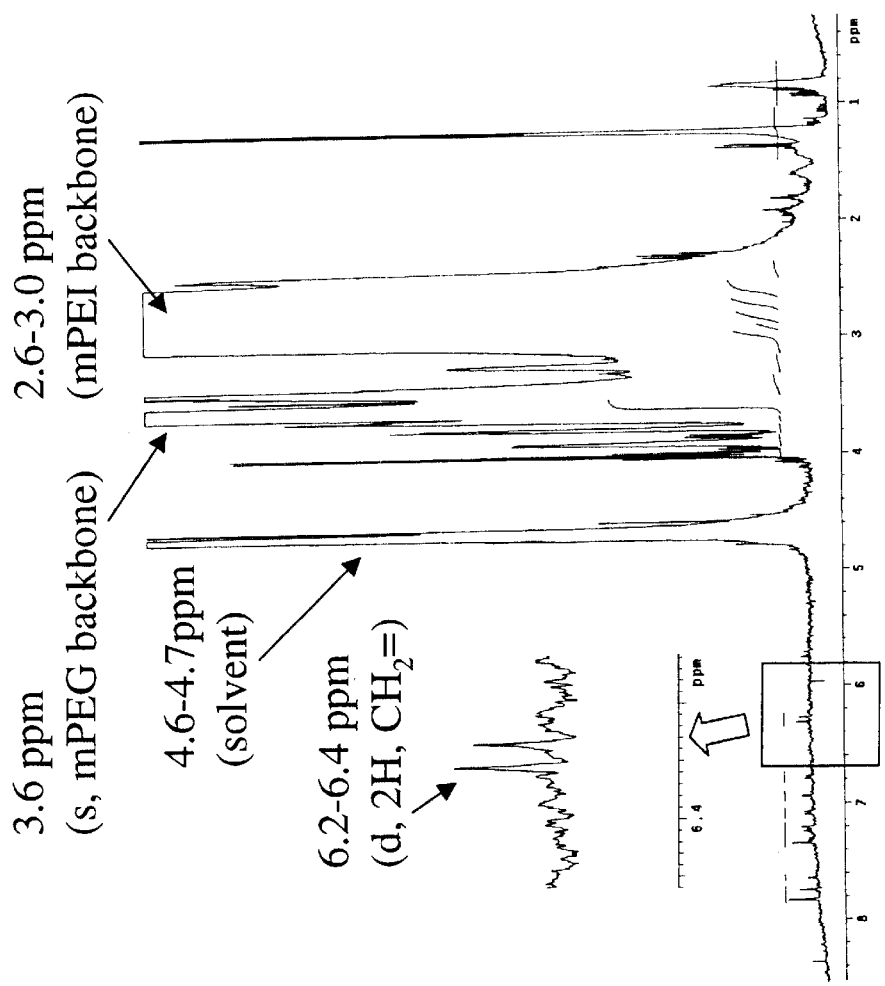
FIG. 2 is a depiction of an illustrative $^1$H-NMR spectrum (400 $MH_z$) analysis of 1% PEG-PEI in $D_2O$ at a reaction time of 0.5 h and at pH 7.0.
Figure 3:
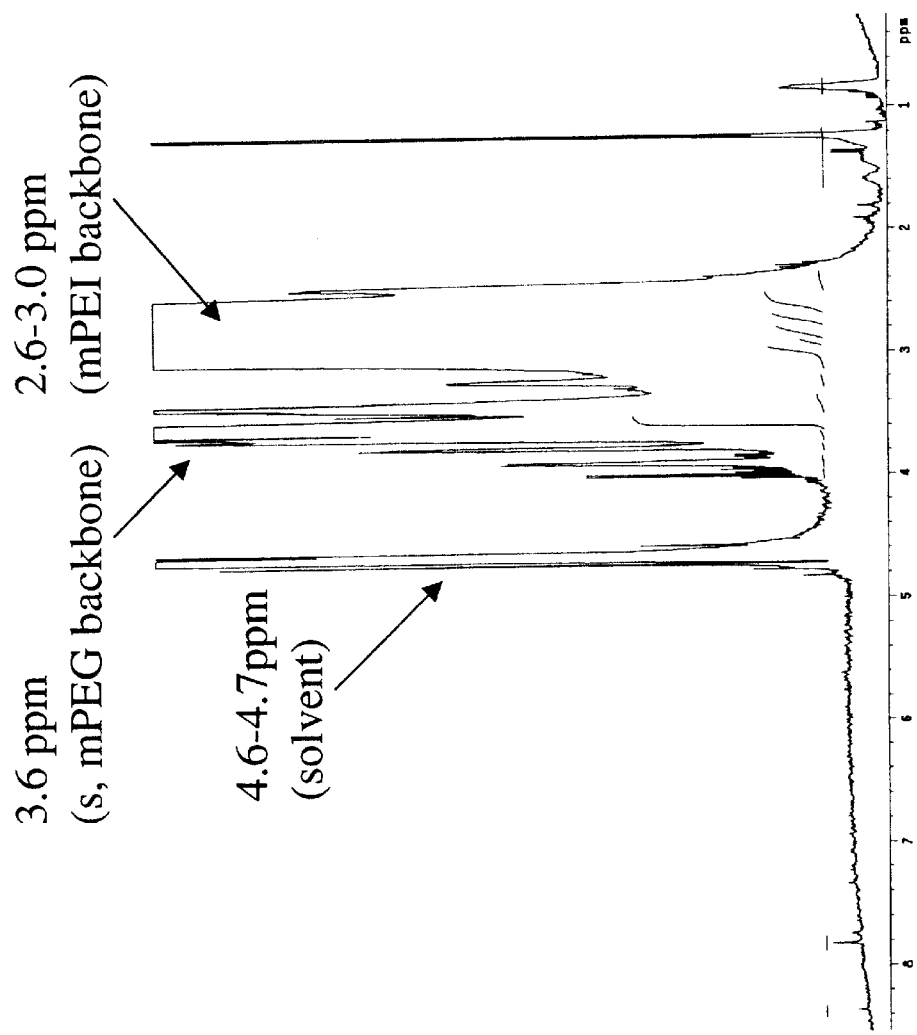
FIG. 3 is a depiction of an illustrative $^1$H-NMR spectrum (400 $MH_z$) analysis of 1% PEG-PEI in $D_2O$ at a reaction time of 2 hrs and at pH 7.0.

Many kinds of bifunctional PEG derivatives have been used to conjugate ligands to a cationic polymer. A bifunctional PEG having a-vinyl sulfone on one terminal and ω-N-hydroxysuccinimidyl ester on the other terminal, namely VS-PEG-NHS, is used in the present invention for coupling PEG with a predetermined mole percent of the amine groups of the cationic polymer by choosing a certain pH for the reaction. The NHS groups can be rapidly conjugated with amine groups of the proteins, peptides or cationic polymer under alkaline conditions at around a pH of 8.0. Therefore, the VS group on the bifunctional PEG derivative can react to the thiol group of proteins or peptides at a pH value less than 8.0 after the conjugation of the NHS group to the amine groups of proteins or peptides. Although the VS groups can react to the amine groups at a pH over 9.0 with a half life of 0.5 h, the reaction is very slow at pH 8.0. To estimate the possibility of controlling the reaction of both NHS and VS groups of the bifunctional VS-PEG-NHS, the reaction kinetics were monitored at pH of 7.0 (FIGS. 2 and 3). Unexpectedly, the $^1$H-NMR determination (FIG. 3) indicated that all the VS groups, after reaction for 2 h, were completely and rapidly bound to the amine groups of PEI as well as the NHS groups regardless of the lower pH values of the reaction medium.

These results demonstrate that it would be difficult to control the selective reaction between the VS and the NHS groups by controlling the reaction conditions such as the pH, the concentration, and the reaction time. In addition, these results suggested that PEI would be cross-linked by VS-PEG-NHS. This behavior seemed to be due to a higher density of amine groups in PEI, which has 581 amine functions if assuming a mean $M_w$ of 43 Da for the repeat unit. The molar ratio of reaction sites of both the VS and the NHS groups to amine groups of PEI was 1:50 when 1% PEG bearing PEI was prepared as shown in FIGS. 2 and 3. On the contrary, the NHS groups of VS-PEG-NHS were selectively and completely conjugated with the amine groups of a small compound such as p-aminophenyl βd-galactopyranoside at a molar ratio of 1:10 at step 1 in FIG. 5. In the next reaction step, the VS groups of VS-PEG-Gal were completely conjugated with the amine groups of PEI as shown in FIG. 2.

In the transfection study with PEI in HepG2 cells, increasing the N/P ratios of PEI decreased the efficiency of transfection, the optimal N/P ratio was found to be 5. These properties of PEI suggests that PEI would cause cytotoxicity at higher N/P ratios. For Gal-PEG-PEI derivatives, the expression with 1% Gal-PEG-PEI was higher with increased N/P ratios than that of PEI at an N/P of 5, suggesting that cytotoxicity due to cationic charge would be reduced because of the PEG spacer and sugar moieties exposed on the surface of the polymer/pDNA complexes. Unexpectedly, 5% Gal-PEG-PEI showed lower expression at all N/P ratios. From the results of gel retardation studies (FIG. 8), increasing galactosylation decreased the packing capacity. Therefore, the lowest expression would be caused by the dissociation of pDNA before internalization into HepG2 cells.

Based on the reaction properties of VS-PEG-NHS, this invention provides a method for qualitatively and quantitatively conjugating TM-PEG with the amine groups of polyamines such as PEI, which is reproducible and convenient and produces polycationic gene carriers bearing any kind of ligand with amine groups. These new polymeric gene carriers, PEI derivatives with terminally galactose-grafted PEG, retain their potent ability to condense pDNA electrostatically and show sufficient transfection efficiency in HepG2 cells.

The following Examples are presented to illustrate the process of preparing the composition and method of using the composition of the present invention. Branched PEI ($M_w$=25 kDa) was purchased from Aldrich Chemical Company, Inc. (Milwaukee, WI). An α-vinyl sulfone, ω-N-hydroxysuccinimidyl ester type of PEG (VS-PEG-NHS, $M_w$=3534 Da with 3400 Da of PEG chains) was purchased from Shearwater Polymers, Inc. (Huntsville, Ala.). p-aminophenyl βd-galactopyranoside was purchased from Sigma (St. Louis, Mo.). Dialysis tubing (molecular weight cutoff (MWCO) of 1000 and 8000 Da) was purchased from Spectrum (Houston, Tex.). A PD-10 column packed Sephadex G-25 was purchased from Amersham Pharmacia Biotech (Piscataway, N.J.). Plasmid DNA encoding firefly luciferase driven by a cytomegaloviral promoter (pCMVLuc) and a marker dye for gel electrophoresis (Blue/Orange 6X Loading Dye) were purchased from Promega (Madison, Wis.). A molecular weight ladder of pDNA (1 kb DNA Ladder) was purchased from Gibco BRL (Grand Island, N.Y.).

For other reagents, commercial special grade reagents were used without further purification.

EXAMPLE 1

Effect of pH on Conjugation of VS-PEG-NHS to Amine Groups of PEI

Branched PEI ($M_w$=25 kDa) (0.02 mmol: 0.5 g) was dissolved in 10 mL of 0.05 M Na, K phosphate buffer and adjusted to pH 6.0, 7.0, and 8.0, by addition of 6 N HCl. The branced PEI has 581 amine functions per molecule and a mean $M_w$ of 43 Da for the repeat unit, according to M. A. Zanta, O. Boussif, A. Adib, J. P. Behr, In vitro gene delivery to hepatocytes with galactosylated polyethylenimine. Bioconjugate Chem. 8 (1997) 839–844. 5.81 μmol of VS-PEG-NHS, which is equivalent of 1 molar percent of amine groups of the PEI, was dissolved in 1 mL of anhydrous dimethylene sulfoxide (DMSO), which was then added into 0.5 mL of each PEI solution containing 1 μmol of PEI and reacted at room temperature for up to 2 hours. The product was purified by dialysis against distilled water (dialysis tubing with MWCO 8000 Da) and freeze-dried. The reaction rate needed to conjugate the VS groups of VS-PEG-NHS to the amine groups of PEI was estimated at between 0.5 and 2 h in the PEI solution containing 0.02 mmol/100 mL at pH 7.0. The molar ratios of PEG to PEI in the product were calculated from $^1$H-NMR using a Varian Unity-Plus 400 $MH_z$ Spectroscopy. Samples were prepared by dissolving the products into deuterium oxide.

EXAMPLE 2

Conjugation of VS-PEG-NHS to Amine Groups of p-Aminophenyl βd-Galactopyranoside 10 excess moles of p-aminophenyl βd-galactopyranoside (0.50 mmol: 135.65 mg) were added to 176.7 mg of VS-PEG-NHS (0.05 mmole) dissolved in 1 mL of anhydorous N, N-dimethylformamide (DMF). This solution was added to 0.05 mmol of VS-PEG-NHS dissolved in 1.5 mL of anhydrous DMF and reacted by gentle stirring for 6 hours at room temperature under nitrogen. The product (VS-PEG-Gal) was purified by dialysis against distilled water (dialysis tubing with MWCO 1000 Da) and freeze-dried. The reproducibility of this step was confirmed with different batches ranging from 0.0125 to 0.14 mmol of VS-PEG-NHS.

The molar ratio of galactose to PEG in the product was calculated from $^1$H-NMR using a Varian Unity-Plus 400 $MH_z$ Spectroscopy. Samples were prepared by dissolving the products into deuterium oxide($D_2O$).

EXAMPLE 3

Synthesis of PEI with 1 and 5% of Terminally Galactose-Grafted PEG (Gal-PEG-PEI)

In preparing 1% and 5% (mol/mol) conjugation to nitrogen atoms of PEI with the VS groups of PEG, 5.81 and 29.05 mol of VS-PEG-Gal, respectively, were conjugated to 581 mol of amine functions per molecule of PEI. PEI (0.02 mmol: 0.5 g) was dissolved in 10 mL of water and adjusted to pH 7.0 by addition of 6 N HCl. Each molar equivalent of VS-PEG-Gal was dissolved in 20 mL of anhydrous DMSO, then added into the PEI solution and reacted at room temperature for 24 h. The reaction solution was dialyzed against distilled water (dialysis tubing with MWCO 8000 Da) and loaded on a PD-10 for purification. The fractions containing the products, which were eluted with 2.5 to 6 mL of distilled water, were collected and freeze-dried.

EXAMPLE 4

Characterization of VS-PEG-NHS Reaction Behavior with Amines of PEI and p-Aminophenyl βd-Galactopyranoside A bifunctional PEG, which consists of an α-vinyl sulfone and ω-N-hydroxysuccinimidyl ester types (VS-PEG-NHS), is commercially produced for specific coupling with amine groups and thiol groups in proteins. The $^1$H-NMR spectrum of VS-PEG-NHS is shown in FIG. 1. The peaks at 3.6 ppm, at 4.6–4.7 ppm, and at 6.2–6.4 ppm were distributed to the PEG (s, —$CH_2$—$CH_2$), the solvent ($D_2O$), and the vinyl group (d, =$CH_2$), respectively. The reaction behavior of the VS groups was monitored from the integrity ratio. The conjugation reaction of the NHS groups to the amine groups of PEI were performed at a pH of 6.0 to 8.0 in the reaction medium. However, $^1$H-NMR spectrums after the PEG was grafted to PEI at a pH range of 6.0 to 8.0, showed the complete disappearance of the vinyl group. The integrity ratio of PEG and PEI (at 2.6–3.0 ppm) indicated complete pegylation.

To monitor the reaction kinetics of the VS groups in detail, the integrity ratio changes under pH 7.0 were determined at 0.5 and 2 h at a 10-fold diluted concentration of PEI to suppress the reaction efficiency as compared with the preliminary study. As shown in FIGS. 2 and 3, only 22 mol % of the VS groups remained at 0.5 h and the peaks of the VS groups completely disappeared at 2 h. This behavior suggested that the VS groups could be easily conjugated with the amine groups of PEI as well as with the NHS groups under the pH range of 6.0 to 8.0.

Figure 4:
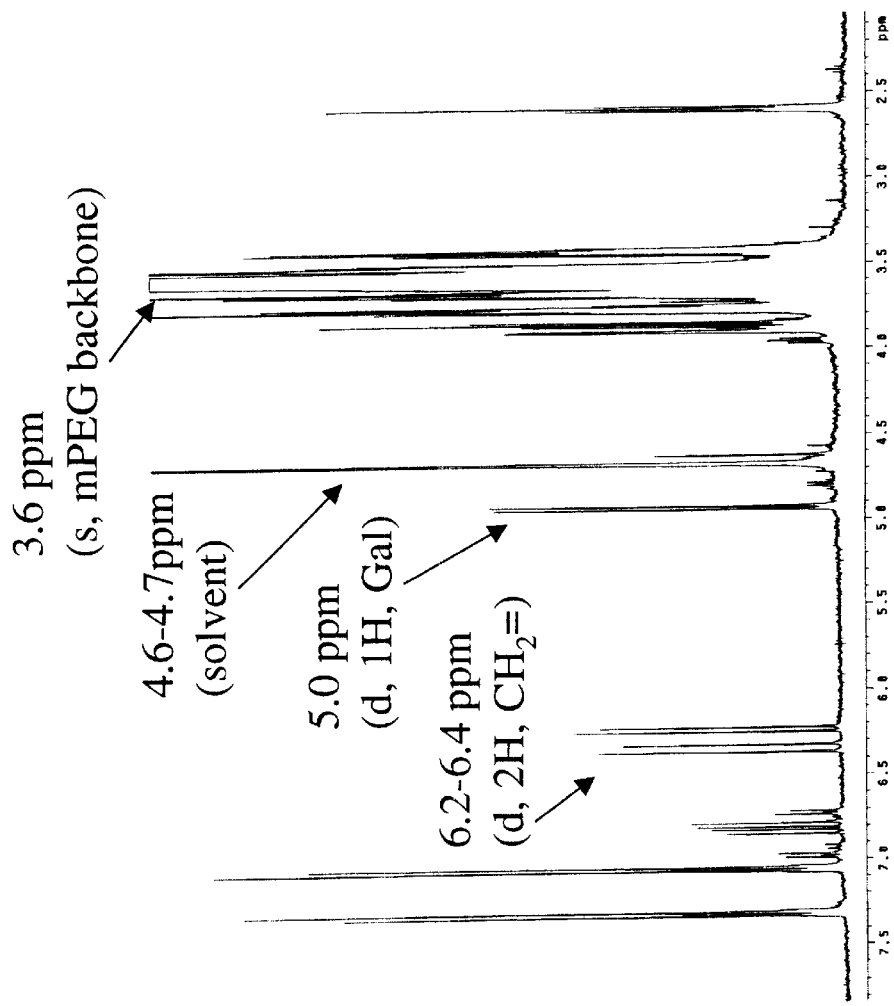
FIG. 4 is a depiction of an illustrative $^1$H-NMR spectrum (400 $MH_z$) analysis of VS-PEG-Gal in $D_2O$.

The $^1$H-NMR spectrum after conjugating p-aminophenyl βd-galactopyranoside with VS-PEG-NHS is shown in FIG. 4. The new peak due to galactose appeared at 4.9 ppm. From the integrity ratio of galactose and PEG, the galactosylated percentages were 80 and 96 mol % at 2 and 6 h, respectively. However, the peaks of the VS groups remained present at 6 h.

Based on the different reaction behavior of VS-PEG-NHS with polyamines or monoamines, the synthesis scheme of Gal-PEG-PEI derivatives is shown in FIG. 5. Only two steps of coupling reactions were necessary to produce Gal-PEG-PEI. The galactosylated percentage, the remaining percentage of VS at Step 1 and the total yield percentage with three batches were 98.0±2.2%, 97.4±3.1%, and 47.2±6.2%, respectively. The synthesis of terminal galactose-grafted PEG was reproducible.

Figure 6:
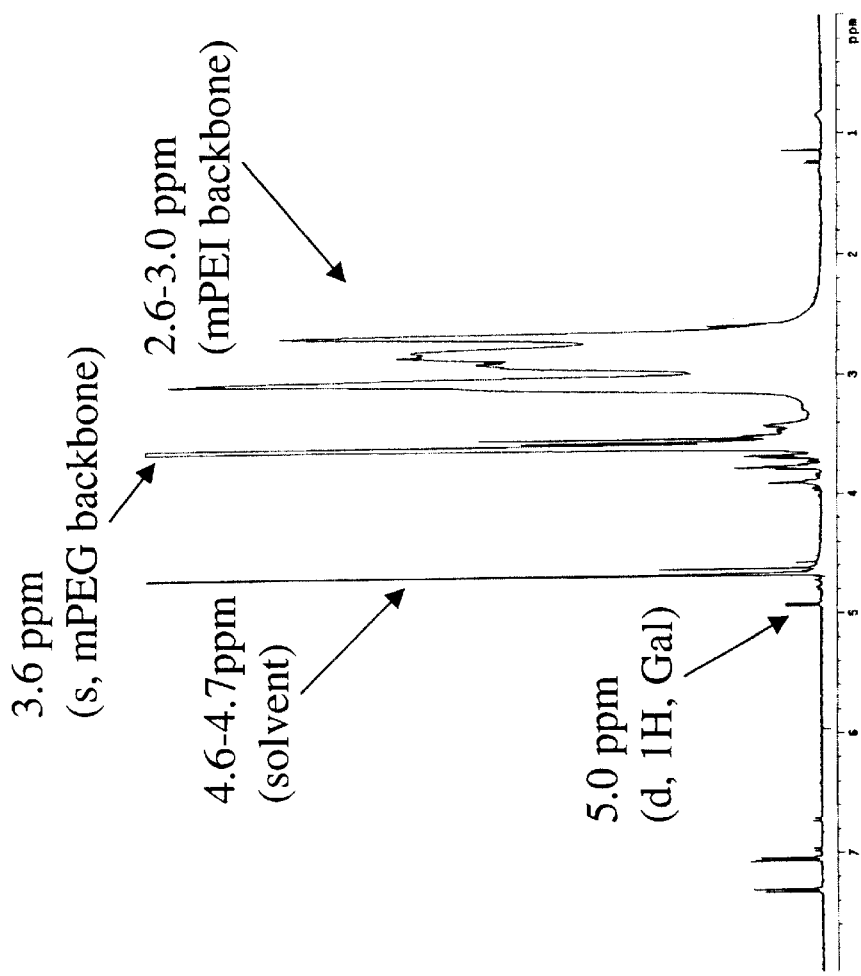
FIG. 6 is a depiction of an illustrative $^1$H-NMR spectrum (400 $MH_z$) analysis of 1 mole % Gal-PEG-PEI (wherein 1 mole % of the amine groups of PEI are grafted with Gal-PEG).
Figure 7:
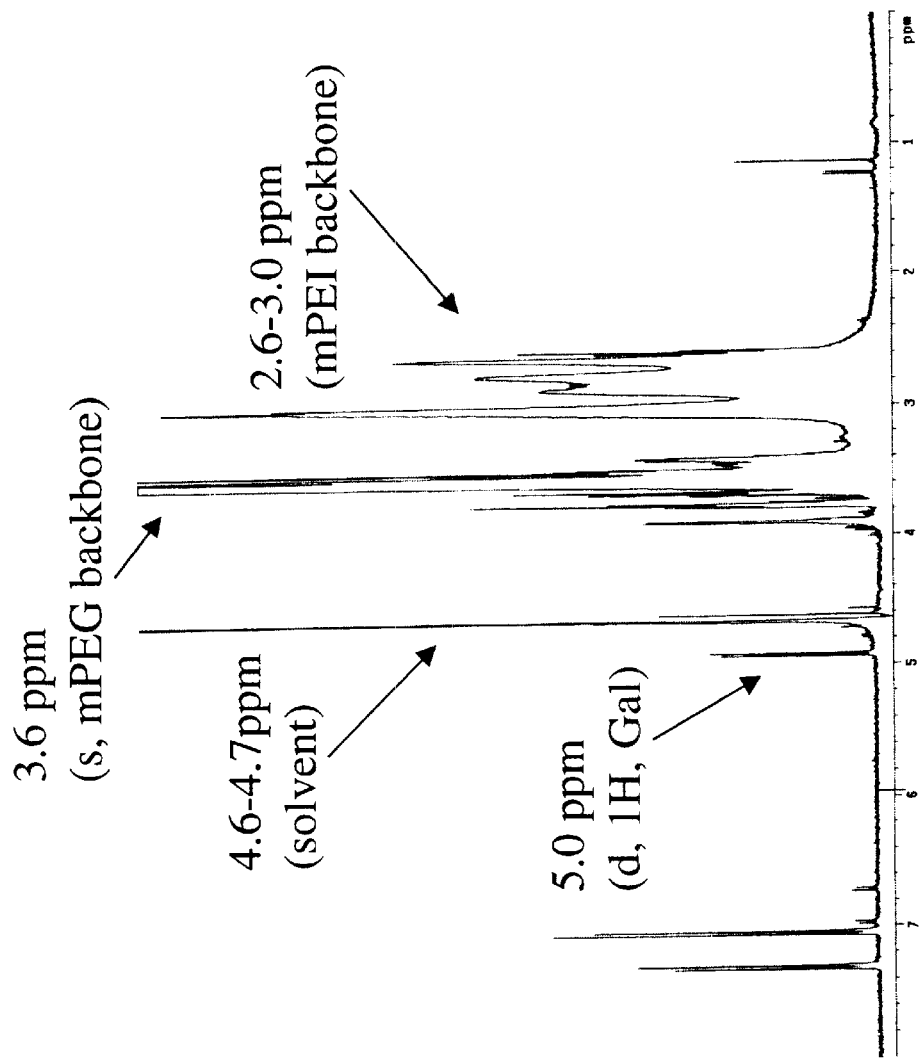
FIG. 7 is a depiction of an illustrative $^1$H-NMR spectrum (400 $MH_z$) analysis of 5 mole % Gal-PEG-PEI(wherein 5 mole % of the amine groups of PEI are grafted with Gal-PEG).

The $^1$H-NMR spectrums of Gal-PEG-PEI are shown in FIGS. 6 and 7. From the integrity ratio of galactose and PEI, the galactosylation was 1 and 5 mol % to amine functional group of PEI. At the second step, the pre-designed contents of galactose could be completely conjugated to PEI.

EXAMPLE 5

Gel Retardation Assay of 1 and 5% Gal-PEG-PEI/pDNA Complexes

Experiments were performed to investigate whether the Gal-PEG-PEI composition according to the present invention formed complexes with pCMVLuc. Ten microliters of pCMVLuc solution (25 µg/mL in 5% (w/v) sucrose, 20 mM HEPES buffer, pH 7.4) was added to 10 µL of various amounts of 1 and 5% Gal-PEG-PEI solution (5% (w/v) sucrose, 20 mM HEPES buffer, pH 7.4) and incubated for 0.5 h at 37. After addition of 4 µL of loading dye into each complex solution, 10 µL of this solution was loaded in a well of 1% agarose gel in 89 mM Tris-Boric acid containing 2 mM EDTA and electrophoresed at 80 V for 1 h. The visualization of pDNA was illuminated with ethidium bromide (0.5 µg/mL). A 1 kb DNA Ladder, which consisted of 12 fragments ranging from 1018 bp to 12216 bp, was used as a DNA marker.

It was observed that complexes between two Gal-PEG-PEI derivatives and pDNA were formed at N/P ratios of 1, 5, 10, 20, and 30. The complexes with PEI were formed at N/P ratios of 1, 5, and 10. The N/P ratios showed the molar ratios of amine functions of PEI or Gal-PEG-PEI to phosphate functions of pDNA by assuming that 1 and 5% of 581 amine functions per molecule of PEI were conjugated with terminally galactose-grafted PEG respectively and that 1 µg of pDNA has 3 nmol of phosphate functions with a mean $M^w$ of 330 Da for nucleic acids.

Figure 8:
FIG. 8 shows an illustrative band retardation assay using 1% agarose in 89 mM Tris-Boric acid containing 2 mM EDTA. Lane 1:1 KB DNA Ladder; Lane 2: DNA(1 µg); Lane 3-5: DNA(N) and PEI(P) with an N/P ratio of 1,5, and 10 respectively; Lane 6-10: DNA(N) and 1 mole % Gal-PEG-PEI(P) with an N/P ratio of 1, 5, 10, 20, and 30 respectively; Lane 11-15:DNA(N) and 5 mole % Gal-PEG-PEI(P) with an N/P ratio of 1, 5, 10, 20, and 30 respectively.

The interaction between two Gal-PEG-PEI derivatives and pDNA was compared with that of PEI alone. As shown in FIG. 8, 1% Gal-PEG PEI showed complete retardation at an N/P ratio of 5 or more, indicating that the interaction properties with pDNA were not influenced by the conjugation with 1% Gal-PEG to PEI. No migration of pDNA by gel electrophoresis indicates that all amounts of the negatively charged pDNA were complexed with positively charged PEI derivatives at this ratio. On the contrary, the pDNA with 5% Gal-PEG-PEI at an N/P ratio of 5 was detected in the well, which suggested incomplete condensation.

The best conditions for an in vitro transfection study would be at an N/P ratio of 5 for 1% Gal-PEG-PEI and 10 for 5% Gal-PEG-PEI.

EXAMPLE 6

Trasfection Assays of 1 or 5% grafted Gal-PEG-PEI

The in vitro transfection efficiency of GaL-PEG-PEI, synthesized according to Example 5, was evaluated using the HepG2 cell line. HepG2 (human hepatocarcinoma cells, ATCC, No.HB-8065) was grown in Dulbecco's Modified Eagles Medium (DMEM) supplemented with 10 fetal bovine serum (heat-inactivated at 56 for 0.5 h) at 37° C. under humidified 5% $CO_2$. The cultured HepG2 cells were seeded on a 24-well plate at an initial density of 20,000–50,000 cells/well 24 h prior to transfection. All experiments were done in triplicate.

To prepare polymer/pCMVLuc complexes, 2 µg of pDNA (25 µg/mL in 5% (w/v) sucrose, 20 mM HEPES buffer, pH 7.4) were mixed with the same volume of various polymer amounts dissolved in 5% (w/v) sucrose, 20 mM HEPES buffer, pH 7.4 for 0.5 h at 37° C.

For the transfection, cells were incubated in 160 µL of polymer/pCMVLuc complexes solution containing 2 µg of pCMVLuc and PEI at N/P ratios of 1, 5, or 10. Cells were also incubated in 160 µL of polymer/pCMVLuc complexes solution containing 2 µg of pCMVLuc and 1 or 5% Gal-PEG-PEI at N/P ratios of 1, 5, 10, 20, or 30. The cells were then incubated with 340 µL of serum-free DMEM for 4 hours, the medium was then removed and replaced by fresh growth medium containing 10% FBS. The cells were incubated for an additional 20 hours.

After transfection proceeded for 24 hours, the culture medium was discarded and the cells were washed twice with 1 mL of $Ca^{2+}$, $Mg^{2+}$-free phosphate buffer saline. The cells were incubated for 0.5 h on ice with 100 µL of Lysis Reagent 1X (Promega, Madison, Wis.). The lysate was centrifuged at room temperature for 2 min at 14,000 rpm. Twenty microliters of lysate was put into each well of a 96-well plate, and diluted with 100 µL of luciferase reaction buffer (Promega, Madison, Wis.), and the luminescence was measured for 10 sec (Dynex Technologies Inc., Chantilly, Va.). The results were expressed as relative light units (RLU) per milligram of cell protein. Protein concentration per well was measured by a BCA protein assay (Pierce Rockford, Ill.). The statistical significance of the results was evaluated by the Student's t-test for the transfection study.

Figure 9:
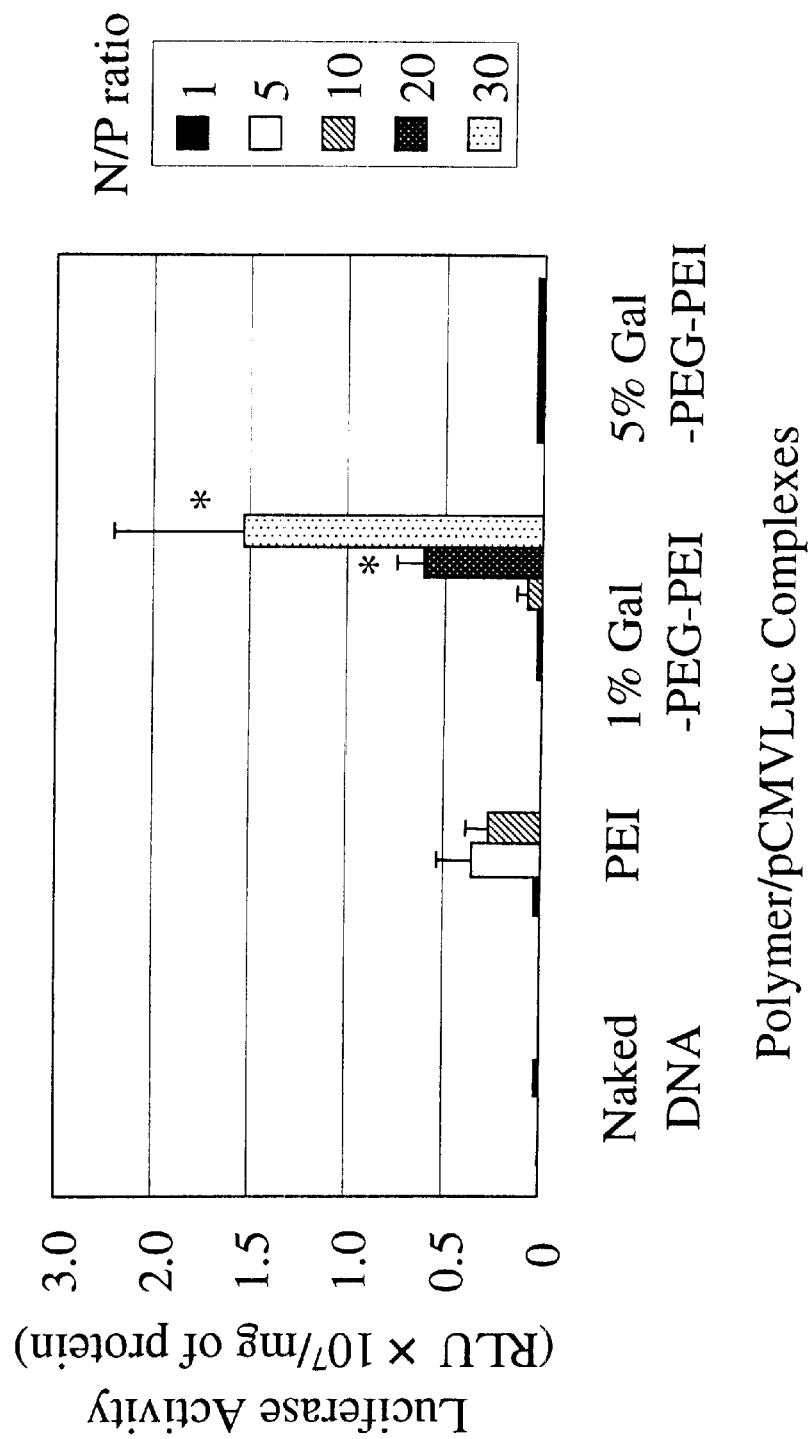
FIG. 9 is a graphical representation showing the results of transfection experiments using PEI, 1 mole % Gal-PEG-PEI and 5 mole % Gal-PEG-PEI at various N/P ratios.

The transfection properties of Gal-PEG-PEI derivatives were compared with those of PEI in HepG2 cells as human hepatocyte models (FIG. 9). While transfection with naked DNA was very low ($4.8 \times 10^4$ RLU/mg of protein), the complexes with PEI at an N/P ratio of 5 showed a 725-fold increase in transfection efficiency with a plateau at an N/P ratio of 10. For 1% Gal-PEG-PEI, the gene expression at an N/P ratio of 5 was low ($9.1 \times 10^4$ RLU/mg of protein) but increased with increasing N/P ratios. The mean values of luciferase activity of 1% Gal-PEG-PEI reached up to 1.7 and 4.4-fold at N/P ratios of 20 and 30, respectively, as compared with that of PEI at an N/P ratio of 5. The transfection efficiency of N/P ratios of 20 and 30 were significantly higher than of PEI at an N/P ratio of 10, though there was shown no significant difference from that of PEI at an N/P ratio of 5. However, unexpectedly, 5% Gal-PEG-PEI showed lower transfection efficiency at all the N/P ratios (less than $2.6 \times 10^4$ RLU/mg of protein).

Therefore, the present invention provides a new method of synthesis of PEI derivatives with 1 and 5% terminal galactose-grafted PEG (Gal-PEG-PEI) which protect against aggregation under physiological conditions and still bear sufficient targeting sugar moieties. The reaction kinetics of both NHS and VS groups of the bifunctional VS-PEG-NHS were monitored at pH of 7.0 (FIGS. 2 and 3). Unexpectedly, the $^1$H-NMR determination (FIG. 3) indicated that all the VS groups, after reaction for 2 h, were completely and rapidly bound to the amine groups of PEI as well as the NHS groups regardless of the lower pH values of the reaction medium.

These results demonstrate that the NHS groups of VS-PEG-NHS were selectively and completely conjugated with the amine groups of a small compound such as p-aminophenylβd-galactopyranoside at a molar ratio of 1:10 at step 1 in FIG. 5. In the next reaction step, the VS groups of VS-PEG-Gal were completely conjugated with the amine groups of PEI as shown in FIG. 2.

In the transfection study with PEI in HepG2 cells, increasing the N/P ratios of PEI decreased the efficiency of transfection, the optimal N/P ratio was found to be 5. These properties of PEI were similar to the reported data, suggesting that PEI would cause cytotoxicity at higher N/P ratios.

For Gal-PEG-PEI derivatives, the expression with 1% Gal-PEG-PEI was higher with increased N/P ratios than that of PEI at an N/P of 5, suggesting that cytotoxicity due to cationic charge would be reduced because of the PEG spacer and sugar moieties exposed on the surface of the polymer/pDNA complexes. Unexpectedly, 5% Gal-PEG-PEI showed lower expression at all N/P ratios. From the results of gel retardation studies (FIG. 8), increasing galactosylation decreased the packing capacity. Therefore, the lowest expression would be caused by the dissociation of pDNA before internalization into HepG2 cells.

Therefore, this invention provides a method for qualitatively and quantitatively conjugating TM-PEG with the amine groups of polyamines such as PEI, which is reproducible and convenient and produces polycationic gene carriers bearing any kind of ligand with amine groups. These new polymeric gene carriers, PEI derivatives with terminally galactose-grafted PEG, retain their potent ability to condense pDNA electrostatically and show sufficient transfection efficiency in HepG2 cells.

The above Examples are presented for illustrative purposes only and are not intended, and should not be construed to limit the invention in any manner. Various modifications of the compounds and methods of the invention may be made without departing from the spirit or scope thereof and it is to be understood that the invention is intended to be limited only as defined in the appended claims.

I claim:

1. A polymeric conjugate that functions as a gene carrier comprising a cationic polymer(CP) member grafted with a poly(ethylene glycol) member (PEG), which is in turn covalently bound to a targeting moiety(TM), wherein 0.1 to 10 mole percent of the cationic groups of said CP are substituted with said TM-PEG, said polymeric conjugate is synthesized by a process comprising: 1) obtaining a TM having one functional amine group or adding one functional amine group to the TM and a bifunctional PEG containing a $\lambda$-vinyl sulfone(VS) at one terminal and a $\omega$-N-hydroxysuccinimidyl ester(NHS) at the other terminal(VS-PEG-NHS); 2) reacting the amine group of the TM with the NHS group of the VS-PEG-NHS to obtain VS-PEG-TM; and 3) reacting the VS group of the VS-PEG-TM with the amine groups of the CP at a pH of 4 to 9 to obtain CP-PEG-TM.

2. The polymeric conjugate of claim 1 wherein said PEG has molecular weight between 0.25 and 35K Daltons.

3. The polymeric conjugate of claim 1 wherein said CP has molecular weight between 1.8K and 800K Daltons.

4. The polymeric conjugate of claim 1 wherein said CP is a member selected from the group consisting of polyamine (PA), polylysine(PLL), polyalkylenimine(PAI) and polyethylenimine(PEI).

5. The polymeric conjugate of claim 4 wherein said CP is a member selected from the group consisting of polyamine (PA), polyalkylenimine(PAI) and polyethylenimine(PEI).

6. The polymeric conjugate of claim 5 wherein said CP is polyethylenimine(PEI).

7. The polymeric conjugate of claim 1 wherein said TM is a targeting member selected from the group consisting of monosaccharides, oligosaccharides, terminal sugar residues, polysaccharides, terminal monoglycosides, targeting peptides, and antibodies.

8. The polymeric conjugate of claim 7 wherein said TM is galactose, N-acethylgalactosamine, lactose, linear di-, tri- or tetra-galactose, di, tri- or tetra-fructose or mannose terminal monoglycosides.

9. A polymeric conjugate that functions as a gene carrier comprising a polyamine(PA) grafted with a poly(ethylene glycol) member (PEG), which is in turn covalently bound to a targeting moiety(TM), said polymeric conjugate is synthesized by a process comprising: 1) obtaining a TM having one functional amine group or adding one functional amine group to the TM and a bifunctional PEG containing a $\lambda$-vinyl sulfone(VS) at one terminal and a $\omega$-N-hydroxysuccinimidyl ester(NHS) at the other terminal(VS-PEG-NHS); 2) reacting the amine group of the TM with the NHS group of the VS-PEG-NHS to obtain VS-PEG-TM; and 3) reacting the VS group of the VS-PEG-TM with the amine groups of the CP at a pH value between 4 to 9 to obtain CP-PEG-TM.

10. The polymeric conjugate of claim 9 wherein said PA is polyalkylenimine(PAI) or polyethylenimine(PEI).

11. The polymeric conjugate of claim 9 wherein said TM is a targeting member selected from the group consisting of monosaccharides, oligosaccharides, terminal sugar residues, polysaccharides, terminal monoglycosides, targeting peptides, and antibodies.

12. The polymeric conjugate of claim 11 wherein said TM is galactose, N-acethylgalactosamine, lactose, linear di-, tri- or tetra-galactose, di-, tri- or tetra-fructose or mannose terminal monoglycosides.

13. A polymeric conjugate that functions as a gene carrier comprising a PEI member grafted with a poly(ethylene glycol) member (PEG), which is in turn covalently bound to a targeting moiety(TM), wherein 0.1 to 10 mole percent of the amine groups of said PEI are substituted with said TM-PEG, and said polymeric conjugate is synthesized by a process comprising:

1) obtaining a TM having one functional amine group or adding one functional amine group to the TM and a bifunctional PEG-containing $\lambda$-vinyl sulfone(VS) at one terminal and a $\omega$-N-hydroxysuccinimidyl ester (NHS) at the other terminal(VS-PEG-NHS); 2) reacting the amine group of the TM with the NHS group of the VS-PEG-NHS to obtain VS-PEG-TM; and 3) reacting the VS group of the VS-PEG-TM with the amine groups of the PEI at a pH of 4 to 9 to obtain the PEI-PEG-TM.

14. The polymeric conjugate of claim 13 wherein said TM is a targeting member selected from the group consisting of monosaccharides, oligosaccharides, terminal sugar residues, polysaccharides, terminal monoglycosides, targeting peptides, and antibodies.

15. The polymeric conjugate of claim 14 wherein said TM is galactose, N-acethylgalactosamine, lactose, linear di-, tri- or tetra-galactose, di-, tri- or tetra-fructose or mannose terminal monoglycosides.

16. A method of synthesizing a polymeric conjugate that functions as a gene carrier comprising a polyamine(PA) grafted with a poly(ethylene glycol) member (PEG), which is in turn covalently bound to a targeting moiety(TM), comprising:

1) obtaining a TM having one functional amine group or adding one functional amine group to the TM and a bifunctional PEG containing a $\lambda$-vinyl sulfone(VS) at one terminal and a $\omega$-N-hydroxysuccinimidyl ester (NHS) at the other terminal(VS-PEG-NHS);

2) reacting the amine group of the TM with the NHS group of the VS-PEG-NHS to obtain VS-PEG-TM; and 3) reacting the VS group of the VS-PEG-TM with the amine groups of the CP at a pH of 4 to 9 to obtain CP-PEG-TM.

17. The method of claim 16 wherein said PEG has molecular weight between 0.25 and 35K Daltons.

18. The method of claim 16 wherein 0.1 to 10 mole percent of the amine groups of said PA are grafted with a TM-PEG.

19. The method of claim 16 wherein said PA has molecular weight between 1.8K and 800K Daltons.

20. The method of claim 16 wherein said PA is polyalkylenimine(PAI) or polyethylenimine(PEI).

21. The method of claim 20 wherein said PA is polyethylenimine(PEI).

22. The method of claim 16 wherein said TM is a targeting member selected from the group consisting of monosaccharides, oligosaccharides, terminal sugar residues, polysaccharides, terminal monoglycosides, targeting peptides, and antibodies.

23. The method of claim 22 wherein said TM is galactose, N-acethylgalactosamine, lactose, linear di-, tri- or tetra-galactose, di-, tri-, tetra- fructose or mannose terminal monoglycosides.

24. A composition for efficiently transfecting a targeted cell comprising a nucleic acid(N) and a polymeric conjugate (P) comprising a cationic polymer(CP) member grafted with a poly(ethylene glycol) member (PEG), which is in turn covalently bound to a targeting moiety(TM), wherein 0.1 to 10 mole percent of the cationic groups of said CP are substituted with said TM-PEG, said polymeric conjugate is synthesized by a process comprising:

1) obtaining a TM having one functional amine group or adding one functional amine group to the TM and a bifunctional PEG containing a $\lambda$-vinyl sulfone(VS) at one terminal and a $\omega$-N-hydroxysuccinimidyl ester (NHS) at the other terminal(VS-PEG-NHS); 2) reacting the amine group of the TM with the NHS group of the VS-PEG-NHS to obtain VS-PEG-TM; and 3) reacting the VS group of the VS-PEG-TM with the amine groups of the CP at a pH of 4 to 9 to obtain CP-PEG-TM.

25. The composition of claim 24, wherein the N/P ratio is within a range of 2 to 30.

26. The composition of claim 25, wherein the N/P ratio is within a range of 5 to 20.

27. A composition for efficiently transfecting a targeted cell comprising a nucleic acid(N) and a polymeric conjugate (P) comprising a PEI member grafted with a poly(ethylene glycol) member (PEG), which is in turn covalently bound to a targeting moiety(TM), wherein 0.1 to 10 mole percent of the amine groups of said PEI are substituted with said TM-PEG, and said polymeric conjugate is synthesized by a process comprising:

1) obtaining a TM having one functional amine group or adding one functional amine group to the TM and a bifunctional PEG containing a $\lambda$-vinyl sulfone(VS) at one terminal and a $\omega$-N-hydroxysuccinimidyl ester (NHS) at the other terminal(VS-PEG-NHS); 2) reacting the amine group of the TM with the NHS group of the VS-PEG-NHS to obtain VS-PEG-TM; and 3) reacting the VS group of the VS-PEG-TM with the amine groups of the PEI at a pH of 4 to 9 to obtain PEI-PEG-TM.

28. The composition of claim 27, wherein the N/P ratio is within a range of 2 to 30.

29. The composition of claim 28, wherein the N/P ratio is within a range of 5 to 20.

* * * * *